United States Patent [19]
Schwartz

[11] Patent Number: 5,700,461
[45] Date of Patent: Dec. 23, 1997

[54] METHOD FOR INHIBITING HIV REPLICATION USING IL-4

[75] Inventor: Jerome Schwartz, New York, N.Y.

[73] Assignee: Schering Corporation, Kenilworth, N.J.

[21] Appl. No.: 387,719

[22] PCT Filed: Aug. 17, 1993

[86] PCT No.: PCT/US93/07587

§ 371 Date: Feb. 16, 1995

§ 102(e) Date: Feb. 16, 1995

[87] PCT Pub. No.: WO94/04179

PCT Pub. Date: Mar. 3, 1994

Related U.S. Application Data

[63] Continuation-in-part of Ser. No. 932,134, Aug. 19, 1992, abandoned.

[51] Int. Cl.$^6$ .................................................. A61K 38/20
[52] U.S. Cl. .................... 424/85.2; 514/2; 514/8; 514/12; 514/885
[58] Field of Search .................. 424/85.1, 85.2; 514/2, 8, 12, 885

[56] References Cited

U.S. PATENT DOCUMENTS 4,724,232  2/1988  Rideout et al. ............................ 514/50
5,011,829  4/1991  Hirsch et al. ............................. 514/50

FOREIGN PATENT DOCUMENTS

HEI2-485  1/1990  Japan .
WO9114450  10/1991  WIPO .

OTHER PUBLICATIONS

P. Mertz et al. (1996) Cellular Immunology, vol. 173, pp. 252–260.

PCT/US91/05477; Int'l. Pub Date: 20 Feb. 1992; Title: "Interleukin-4 and Interleukin-1β Synergistically Induce VCAM-1"; Inventors:Masinovsky et al.

PCT/EP91/02380; Int'l. Pub. Date: 25 Jun. 1992; Title: "Pharmaceutical Compositions for the Treatment of B–Cell Malignancies"; Inventors: Banchereau et al.

PCT/US91/07234; Int'l. Pub. Date: 16 Apr. 1992; Title: "Synergism of TNF and IL–4"; Inventor:Aggarwal.

PCT/US91/09167; Int'l Pub. Date: 9 Jul. 1992; Title: "Use of IL–4 to Enhance Immune Response to Immunogens in Vaccines"; Inventors: Rozhon et al.

PCT/US92/00024; Int'l. Pub. Date: 23 Jul. 1992; Title: "Use of IL–4 to Enhance the Reparative Phase of Wound healing and Repair and to Enhance the healing of Infectd Wounds and The Wounds of Diabetic Animals"; Inventors: Schwarz et al.

H. Schuitemaker et al.; "Viral and Cellular Requirements for Replication of HIV in Primary Monocytes", Abstracts of the VII International Conference on AIDS, Florence, 1991, Jun. 16–21;7(1):100 (abstract No. M.A. 1033).

H. Schuitemaker et al., "Proliferation–dependent HIV–1 Infection of Monocytes Occurs during Differentiation into Macrophages", J. Clin. Invest. vol. 89, Apr. 1992, pp. 1154–1160.

Kazazi et al., 1992, *Journal of Gen. Virology* 73:941–949.

Poli and Fauci, 1992, Aids Research & Human Retroviruses 8 (2):191–197.

Hays et al., 1992, Aids 6 (3):265–272.

Fahey et al. (1992) *Clin. Exp. Immunol.* vol. 88, pp. 1–5.

Mosmann et al. (1994) *Science* vol. 265, pp. 193–194.

Fox et al. *Biotechnology* (1994) vol. 12, pp. 128.

*Primary Examiner*—John Ulm
*Assistant Examiner*—Prema Mertz
*Attorney, Agent, or Firm*—James M. Gould; Norman C. Dulak

[57] ABSTRACT

This invention provides a method for inhibiting HIV replication in a patient which comprises administering to a patient infected with HIV a therapeutically effective amount of IL-4.

15 Claims, 1 Drawing Sheet

METHOD FOR INHIBITING HIV REPLICATION USING IL-4

The present application is the United States national application corresponding to International Application No. PCT/US93/07587, filed Aug. 17, 1993, which is a continuation-in-part of U.S. application Ser. No. 07/932,134, filed Aug. 19, 1992, now abandoned, the benefit of which applications are claimed pursuant to the provisions of 35 U.S.C. 120, 363 and 365(c).

This invention relates to a method for inhibiting HIV replication in cells of monocyte/macrophage lineage which employs Interleukin-4.

BACKGROUND OF THE INVENTION

Human immunodeficiency virus (HIV) was initially identified as the etiologic agent of the acquired immunodeficiency syndrome (AIDS) in 1983. Much has been learned subsequently about the structure and function of this virus. In addition, HIV has been shown to be harbored by T helper lymphocytes and cells of monocyte/macrophage lineage [Ho et al., New Engl. J. Med. 321 (24): 1621 (1989)]. The average time interval between the acquisition of HIV infection and the onset of AIDS is approximately 8 to 11 years [Lifson et al., J. Infec. Dis. 158: 1360 (1988)]. This long incubation period suggests that HIV replication is at least partially restricted by host factors.

Mononuclear phagocytes play a prominent role in the pathogenesis of AIDS. These cells are among the first to become infected by HIV. They are also major reservoirs for virus in the central nervous system, lungs and lymph nodes; potential vectors for the spread of virus to different tissues within the infected patient and between individuals; and major regulatory cells that control the pace and intensity of disease progression [Gendelman et al., AIDS 3: 475 (1989)]. Host factors such as Interferon (IFN) that affect viral replication within the mononuclear phagocyte are likely to be major elements in the establishment of restricted virus growth and the delay of HIV disease.

The fact that macrophages are the major virus reservoir in the central nervous system, the lungs, and lymph nodes suggests that therapies that inhibit viral replication in these particular cells may have a major impact on virus burden and disease progression [Gendelman et al., J. Immunol. 145: 2669 (1990)].

Interleukin-4 (IL-4) is a lymphokine that has properties that exemplify many of the characteristics of the set of immune recognition-induced lymphokines [Paul, Blood 77 (9): 1859 (1991)]. IL-4 is principally responsible for the production of IgE in mice in response to a variety of stimuli that elicit Ig class switching to the expression of this Ig class [Finkelman et al., Ann. Rev. Immunol. 8: 303 (1990)]. IL-4 was initially described based on its ability to enhance DNA synthesis by purified resting mouse B lymphocytes stimulated with anti-IgM antibodies [Howard et al., J. Exp. Immunol. 155: 914 (1982)].

IL-4 has also been shown to act on resting B cells to induce expression of class II MHC molecules [Noelle et al., Proc. Natl. Acad. Sci. USA 81: 6149 (1984)], and to enhance the subsequent responsiveness of such cells to anti-IgM antibodies [Rabin et al., Proc. Natl. Acad. Sci. USA 82: 2935 (1985); Oliver et al., Proc. Natl Acad. Sci. USA 82: 2465 (1985)].

Human IL-4 is a glycoprotein that exists in forms having molecular weights between 15,000 and 19,000 daltons. cDNAs encoding both mouse and human IL-4 have been obtained [Lee et al., supra; Noma et al., supra; Yokota et al., Proc. Natl. Acad. Sci. USA 83: 5894 (1986)].

IL-4 has potent effects on T lymphocytes as well as B cells. Resting T cells treated with IL-4 survive in culture without dividing [Hu-Li et al., J. Exp. Med 165: 157 (1987)]. IL-4 also acts on non-lymphoid hematopoietic cells in a variety of ways. It has been shown to inhibit the growth of macrophages [McInnes et al., J. Exp. Med. 167: 598 (1988); Jansen et al., J. Exp. Med. 170: 577 (1989)] and to increase their cytotoxic activity for certain tumor cells [Crawford et al., J. Immunol. 139: 135 (1987)].

Present methods for treating HIV infection which involve the use of AZT, ddI and ddC have not proven to be very effective. There thus is a need for better methods for treating HIV infection.

SUMMARY OF THE INVENTION

The present invention fills this need by providing such a method. More particularly, this invention provides a method for treating HIV infection comprising administering to a patient infected with HIV a therapeutically effective amount of IL-4.

BRIEF DESCRIPTION OF THE FIGURE

This invention can be more readily understood by reference to accompanying FIG. 1, which is a graphical representation of the inhibition of HIV replication in monocytes by various doses of IL-4.

DESCRIPTION OF THE INVENTION

Figure 1:
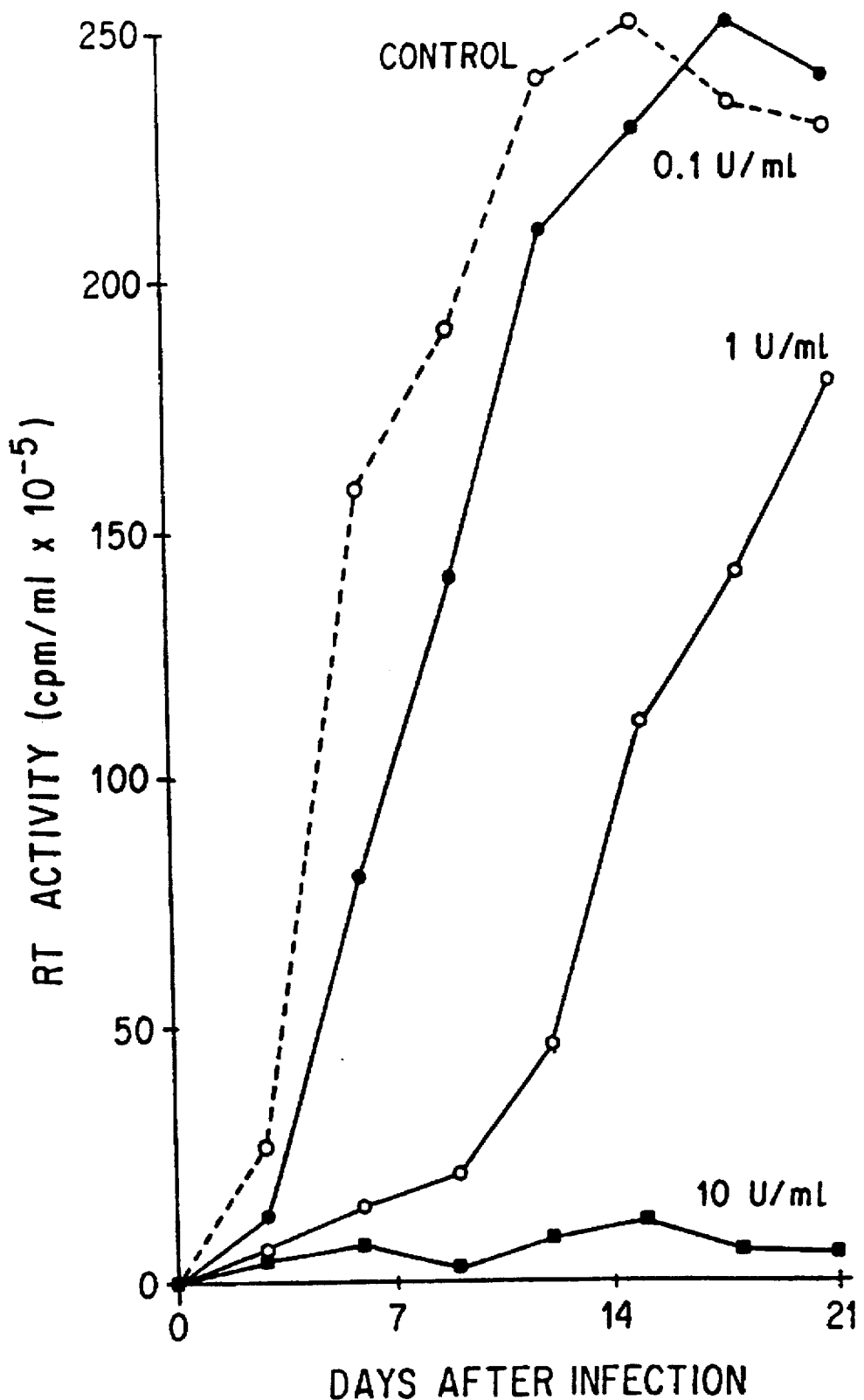

All references cited herein are hereby incorporated in their entirety by reference.

The present invention is directed to the treatment of HIV infection and all conditions resulting from such infection, such as AIDS. Conditions that can be treated by the, methods of this invention are defined herein to include states and levels of morbidity manifested by one or more of the following criteria: (1) seropositivity for HIV virus (and/or HIV antibody), or the presence of intracellular virus particles which can be identified within leukocyte cell isolates by microscopic evaluation; (2) chronic lymphadenopathy as commonly understood in the art; (3) blood T-helper cell count <400/mm$^3$; (4) a demonstrable partial defect in a delayed hypersensitivity response; (5) complete failure to respond to delayed hypersensitivity skin tests and/or the occurrence of thrush.

Patients meeting the above-mentioned criteria are said to have progressed to the "AIDS" classification when, in addition to the above, they become susceptible to opportunistic infections such as cryptococcal meningitis, histoplasmosis, tuberculosis, toxoplasmosis, or PCP (*Pneumocystis carinii* pneumonia). [Redfield et al., "HIV Infection: The Clinical Picture", *The Science of AIDS*, supra, pp.63–73].

The symptoms listed above are illustrative of specific selection criteria to be used in determining candidates for the proposed method of treatment. The effectiveness of treatment can be assessed by monitoring the above-mentioned disease manifestations for abatement. In addition, inhibition of viral replication can be monitored by measurement of the levels of reverse transcriptase in supernatants of infected cell isolates, which is predictive of disease progression. It is well settled that acute phase infection is manifested by high serum titers of virus particles [Coombs et al., New Engl. J. Med. 321 (24): 1626 (1989)].

As used in this invention, the term "HIV" is defined to include both HIV-1 and HIV-2.

As shown herein, the methods of the present invention inhibit HIV replication in cells of monocyte/macrophage lineage. There may, however, be effects on viral replication in other types of cells. There may also be effects on the immune system or other systems. Understanding of the exact mechanism(s) by which IL-4 may act is not essential to this invention.

IL-4 is commercially available from numerous sources, such as Genzyme Corporation, Cambridge, Mass., or it can be prepared by known methods using natural sources or recombinant DNA methodologies [Sheehan et al., Immunol. 142: 884 (1989) and Starnes et al., J. Immunol., 145: 4185 (1990)].

Alternatively, oligonucleotide probe mixtures based on known IL-4 nucleotide sequences can be used to identify DNA encoding IL-4 in genomic or cDNA libraries prepared by standard methods. DNA thus identified can be excised from the library by restriction endonuclease cleavage or prepared using appropriate primers and the polymerase chain reaction (PCR) method [Saiki et al., Science 239: 487 (1988)], sequenced and expressed in a eukaryotic expression system or (following intron deletion by standard methods if necessary) in a prokaryotic or eukaryotic expression system. Of course, both cDNA and genomic DNA libraries can be screened by the application of standard expression cloning methods, instead of by the use of oligonucleotide probes or PCR. IL-4 thus produced is detected through the use of known methods such as immunochemical or bioassay methods.

The IL-4 used will preferably be human recombinant IL-4. It is also preferred that glycosylated IL-4 be used (e.g., recombinant IL-4 produced in a eukaryotic expression system).

In some embodiments of this invention, the IL-4 is administered in combination with one or more other agents known to be effective against HIV, such as 3'-azido-2',3'-dideoxythymidine (AZT), 2',3'-dideoxycytidine (ddC) or 2',3'-dideoxyinosine (ddI).

Pharmaceutical compositions for use in this invention can be supplied in lyophilized form and then reconstituted just prior to use in a pharmaceutically acceptable carrier such as phosphate buffered saline or any of the other well known carriers. The pharmaceutical compositions of the invention can be injected directly into the bloodstream intravenously or via intravenous (i.v.) drip solution, such as Ringer's lactate. Parenteral preparations that can be used include sterile solutions or suspensions. These preparations can be prepared with conventional pharmaceutically acceptable excipients and additives such as stabilizers and carriers. The solutions to be administered may be reconstituted lyophilized powders which may additionally contain, e.g., preservatives, buffers and dispersants. Preferably, the compositions are administered by i.v. injection.

In accordance with the present invention, patients in need of treatment for HIV infection are administered an effective amount of IL-4 to accomplish the above described results. A daily dose of about 0.001 µg/kg body weight to about 50 µg/kg body weight can be administered. More preferably, the daily dose will range from about 0.01 µg/kg body weight to about 10 µg/kg body weight. Most preferably, the daily dose will range from about 0.05 µg/kg body weight to about 2 µg/kg body weight. The precise amount of IL-4 to be administered will be determined by the attending clinician taking into account the etiology and severity of the disease, the patient's condition, age, and other factors.

EXAMPLE

This invention can be illustrated by the following, non-limiting Example.

Methods and Materials

Monocytes were recovered from peripheral blood mononuclear cells (PBMC) of HIV and hepatitis-B seronegative donors after leukapheresis and purified by countercurrent centrifugal elutriation of mononuclear leukocyte-rich fractions of blood cells. Cell suspensions were >98% monocytes by criteria of cell morphology on Wright-stained cytosmears by granular peroxidase and by nonspecific esterase. Monocytes were cultured as adherent cell monolayers ($7.5\times10^{-5/24}$ mm tissue culture well) in 0.5 ml DMEM (formula 78-176AJ, GIBCO, Grand Island, N.Y.) supplemented with 10% heat-inactivated A+ human serum, 50 µg/ml gentamicin (Sigma Chemical Co., St. Louis, Mo.), and 1000 U/ml recombinant human macrophage colony stimulating factor (M-CSF) (Cetus Corp., Emeryville, Calif.). PBMC, isolated from whole blood by Ficoll-diatrizoate (Pharmacia LKB, Piscataway, N.J.) density gradient centrifugation, were cultured at $1\times10^6$ viable cells/ml in RPMI 1640 medium (GIBCO) with 5 µg/ml phytohemagglutinin (PHA) (Sigma), 10% purified human IL-2 (Advanced Biotechnologies Inc., Columbia, Md.), and 15% heat-inactivated fetal calf serum (FCS) (Sterile Systems, Logan, Utah).

PHA/IL-2 treated monocytes were exposed at a multiplicity of infection of 0.01 tissue culture $ID_{50}$/target cell to 4 clinical strains of HIV (GG, YU-2, SM and ADA) originally isolated and passaged in monocytes (AIDS Research and Reference Reagent Program, AIDS Program, NAID, NIH). M-CSF treated monocytes were cultured as adherent monolayers 7 to 10 days before use as target cells. All cultures were refed with fresh medium every 2 to 3 days.

For determination of reverse transcriptase (RT) activity, replicate samples of culture supernatant fluids were added to a reaction mixture of NONIDET P-40® (Sigma), poly(rA) oligo(dT) (Pharmacia, Piscataway, N.J.), dithiothreitol (Pharmacia), $MgCl_2$, and [$\alpha$-$^{32}$P]dTTP (400 Ci/mmol, Amersham Corp., Arlington Heights, Ill.) for 24 h at 37° C. The mixture was applied to chromatography paper, air-dried, and washed five times in 0.3M NaCl-0.03M sodium citrate (pH 7.4) and twice more in 95% ethanol. The paper was dried and cut, and the radioactivity was counted by liquid scintillation spectroscopy. HTLVIIIB served as positive controls for RT activity.

Uninfected or HIV-infected PBMC were grown on plastic substrates in the presence or absence of IL-4. Presence of HIV infection in the cultures was determined by screening cells for plasma membrane-associated and intravacuolar HIV. RT activity was also measured as described above in aliquots of culture supernatant fluids.

Surprisingly, it was found that IL-4 treatment of HIV infected cells resulted in a dose dependent reduction in viral replication following infection. This can be seen in FIG. 1, in which inhibition of viral replication is shown as a reduction in the appearance of the radiolabelled RT in the supernatants (CPMs/ml×$10^{-5}$) in cultures treated with IL-4, as compared to untreated infected cultures (Control). RT levels were measured at numerous time points over the 21 day incubation period. Ten units/ml IL-4 significantly inhibited RT activity for 21 days after infection. This effect was determined by a reduction in the measurable RT activity in the culture supernatants.

The inhibitory effect of IL-4 was freely reversible. Upon removal of IL-4 from the culture system, the levels of viral replication (RT activity) increased to those obtained with untreated HIV infected monocytes.

The specificity of the IL-4 effect on viral replication was confirmed by pre-treatment with monoclonal anti-IL-4 antibodies (data not shown). Inhibition of viral replication in these experiments was not seen in cultures pre-treated with anti-IL-4 antibodies. It was also noted that substitution of media component human sera to fetal calf sera resulted in a decrease in the anti-viral response, perhaps because fetal calf sera contains a number of other constituents that are known to upregulate HIV gene expression that are not found in human sera.

Many modifications and variations of this invention can be made without departing from its spirit and its scope, as will become apparent to those skilled in the art. The specific embodiments described herein are offered by way of example only, and the invention is to be limited only by the terms of the appended claims.

What is claimed is:

1. A method for inhibiting HIV replication comprising administering a therapeutically effective amount of IL-4 to a patient infected with HIV, said effective amount being sufficient to inhibit said replication.

2. The method of claim 1 in which the IL-4 is recombinant human IL-4.

3. The method of claim 2 wherein said effective amount of IL-4 administered is from about 0.001 µg/kg to about 50 µg/kg body weight per day.

4. The method of claim 3 wherein said effective amount of IL-4 administered is from about 0.1 µg/kg to about 10 µg/kg body weight per day.

5. The method of claim 3, wherein said effective amount of IL-4 administered is from about 0.05 µg/kg to about 2 µg/kg body weight per day.

6. The method of claim 1 in which the route of IL-4 administration is systemic.

7. The method of claim 6 in which the mode of systemic administration is selected from the group consisting of intravenous, intraperitoneal, intramuscular, and subcutaneous.

8. The method of claim 1 in which the IL-4 is administered in combination with one or more other agents selected from the group consisting of AZT, ddI, and ddC.

9. A method for inhibiting HIV replication comprising administering a therapeutically effective amount of IL-4 to a patient infected with HIV in combination with one or more other agents selected from the group consisting of AZT, ddI, and ddC.

10. The method of claim 9 in which the IL-4 is recombinant human IL-4.

11. The method of claim 10 wherein said effective amount of IL-4 administered is from about 0.001 µg/kg to about 50 µg/kg body weight per day.

12. The method of claim 11 wherein said effective amount of IL-4 administered is from about 0.1 µg/kg to about 10 µg/kg body weight per day.

13. The method of claim 12 wherein said effective amount of IL-4 administered is from about 0.05 µg/kg to about 2 µg/kg body weight per day.

14. The method of claim 9 in which the route of IL-4 administered is systemic.

15. The method of claim 14 in which the mode of systemic administration is selected from the group consisting of intravenous, intraperitoneal, intramuscular, and subcutaneous.

* * * * *